US009045595B2

(12) United States Patent
Mantelatto et al.

(10) Patent No.: US 9,045,595 B2
(45) Date of Patent: Jun. 2, 2015

(54) PROCESS FOR RECOVERING POLYHYDROXIALKANOATES ("PHAS") FROM CELLULAR BIOMASS

(75) Inventors: Paulo Eduardo Mantelatto, Piracicaba (BR); Alvaro Minto Duzzi, Serrana (BR); Tetuhiko Sato, Sao Paulo (BR); Nazareno Antonio Sertori Durao, Brodowski (BR); Roberto Vianna Nonato, Sao Paulo (BR); Carlo Rocchiccioli, Sao Paulo (BR); Sonia Maria Kesserlingh, Sertaozinho (BR)

(73) Assignee: PHB Industrial S.A., Sao Paulo (BR)

( * ) Notice: Subject to any disclaimer, the term of this patent is extended or adjusted under 35 U.S.C. 154(b) by 1650 days.

(21) Appl. No.: 10/596,077

(22) PCT Filed: Nov. 25, 2004

(86) PCT No.: PCT/BR2004/000237
§ 371 (c)(1),
(2), (4) Date: Aug. 4, 2006

(87) PCT Pub. No.: WO2005/052175
PCT Pub. Date: Jun. 9, 2005

(65) Prior Publication Data
US 2007/0161096 A1 Jul. 12, 2007

(30) Foreign Application Priority Data

Nov. 28, 2003 (BR) .................................. 0306230-9
Nov. 19, 2004 (BR) .................................. 0405622-1

(51) Int. Cl.
C08G 63/90 (2006.01)
C08G 63/89 (2006.01)
C12P 7/62 (2006.01)
C08G 63/06 (2006.01)

(52) U.S. Cl.
CPC ................ *C08G 63/90* (2013.01); *C08G 63/06* (2013.01); *C08G 63/89* (2013.01); *C12P 7/625* (2013.01)

(58) Field of Classification Search
None
See application file for complete search history.

(56) References Cited

U.S. PATENT DOCUMENTS

| 3,044,942 | A |   | 7/1962  | Baptist |       |
|-----------|---|---|---------|---------|-------|
| 3,107,172 | A |   | 10/1963 | Baptist |       |
| 3,275,610 | A |   | 9/1966  | Coty    |       |
| 4,265,770 | A | * | 5/1981  | Thomas ........................ | 210/715 |
| 4,310,684 | A |   | 1/1982  | Vanlautem et al. |  |
| 4,562,245 | A |   | 12/1985 | Stageman et al.  |  |
| 4,705,604 | A |   | 11/1987 | Vanlautem et al. |  |
| 4,968,611 | A | * | 11/1990 | Traussnig et al. ............. | 435/135 |
| 5,213,976 | A | * | 5/1993  | Blauhut et al. ................ | 435/135 |
| 5,536,419 | A | * | 7/1996  | Escalona et al. .............. | 210/767 |
| 5,821,299 | A | * | 10/1998 | Noda ............................. | 524/725 |
| 5,942,597 | A | * | 8/1999  | Noda et al. ................... | 528/361 |
| 5,958,480 | A | * | 9/1999  | Eggink et al. ................... | 426/90 |
| 6,043,063 | A |   | 3/2000  | Kurdikar et al. |  |
| 6,087,471 | A |   | 7/2000  | Kurdikar et al. |  |
| 6,228,934 | B1| * | 5/2001  | Horowitz et al. ............. | 524/800 |
| 6,323,276 | B2| * | 11/2001 | Horowitz et al. ............. | 524/800 |
| 6,368,836 | B2| * | 4/2002  | Horowitz et al. ............. | 435/135 |
| 6,410,096 | B1| * | 6/2002  | Eggink et al. ............. | 427/385.5 |
| 8,357,508 | B2| * | 1/2013  | Mantelatto et al. ............. | 435/41 |

FOREIGN PATENT DOCUMENTS

| EP | 0 014 490  | A2 | 10/1982 |
| EP | 0 036 699  | B2 | 9/1987  |
| EP | 1 455 233  | A2 | 9/2004  |
| WO | WO-95/33065 | A1 | 12/1995 |
| WO | WO-97/07229 | A1 | 2/1997  |
| WO | WO-97/07230 | A1 | 2/1997  |
| WO | WO-98/07879 | A1 | 2/1998  |
| WO | WO-98/46782 | A1 | 10/1998 |
| WO | WO-98/46783 | A1 | 10/1998 |
| WO | WO-01/68890 | A2 | 9/2001  |

OTHER PUBLICATIONS http://en.wikipedia.org/wiki/Flocculation (Apr. 1, 2014).*
http://en.wikipedia.org/wiki/Clarifying_agent (Jan. 1, 2014).*
Nonato R V et al.: "Integrated production of biodegradable plastic, sugar and ethanol"; Applied Microbiology and Biotechnology, vol. 57, No. 1-2, Oct. 2001, pp. 1-5, XP002326949.
Rossell C E V et al.: "Production of biodegradable plastic (PHB), sugar and ethanol in a sugar mill"; International Sugar Journal, vol. 104, No. 1243, 2002, pp. 321-323, XP008046491.
Database CA 'Online! Chemical Abstracts Service, Columbus, Ohio, USA, 1995, Derenzo S et al.; "Extraction of biopolymers from cellular materials", XP002326951 retrieved from STN Database accession No. 123:81739 abstract & BR 9 302 312 A (Cooperativea De Produtores De Cana, Acucar E Alcoa Do Estado De Sao Pa) Feb. 7, 1995.

(Continued)

Primary Examiner — Maury Audet
(74) Attorney, Agent, or Firm — Fish & Richardson P.C.

(57) ABSTRACT

A process for recovering polyhydroxyalkanoates (PHAs) from cellular biomass of bacteria, said biomass being obtained by fermentation and in the form of a cellular biomass slurry in aqueous suspension, comprising the steps of: submitting the slurry to operations of injection of PHA solvent, agitation and heating, in order to form a suspension comprising PHA solvent with the dissolved PHA, water and insoluble residues; recuperating the solvent enriched with PHA; rapidly cooling the solution of PHA solvent to precipitate the dissolved PHA; micro-filtrating the suspension of PHA precipitated in the solvent, in order to separate a paste concentrated with precipitated PHA; washing with water, heating and agitating the concentrated PHA paste, to promote evaporation of the solvent and to obtain a suspension containing PHA granules; agitating and shearing the PHA granules and depleting the residual solvent; and separating the purified PHA particles from the suspension.

33 Claims, 1 Drawing Sheet

(56) References Cited

OTHER PUBLICATIONS

Koninga-De G J M et al.; "Process for the recovery of poly(hydroxyalkanoates) from Pseudomonads. Part 2: Process development and economic evaluation"; Bioprocess Engineering, vol. 17, 1997, pp. 15-21, XP002900486.

International Search Report for International Patent Application PCT/BR2004/000237, date of mailing May 23, 2005.

Braunegg G. et al., "Polyhydroxyalkanoates, biopolyesters from renewable resources: Physiological and engineering aspects", J. Biotech. 65: 127- 161, 1998.

* cited by examiner

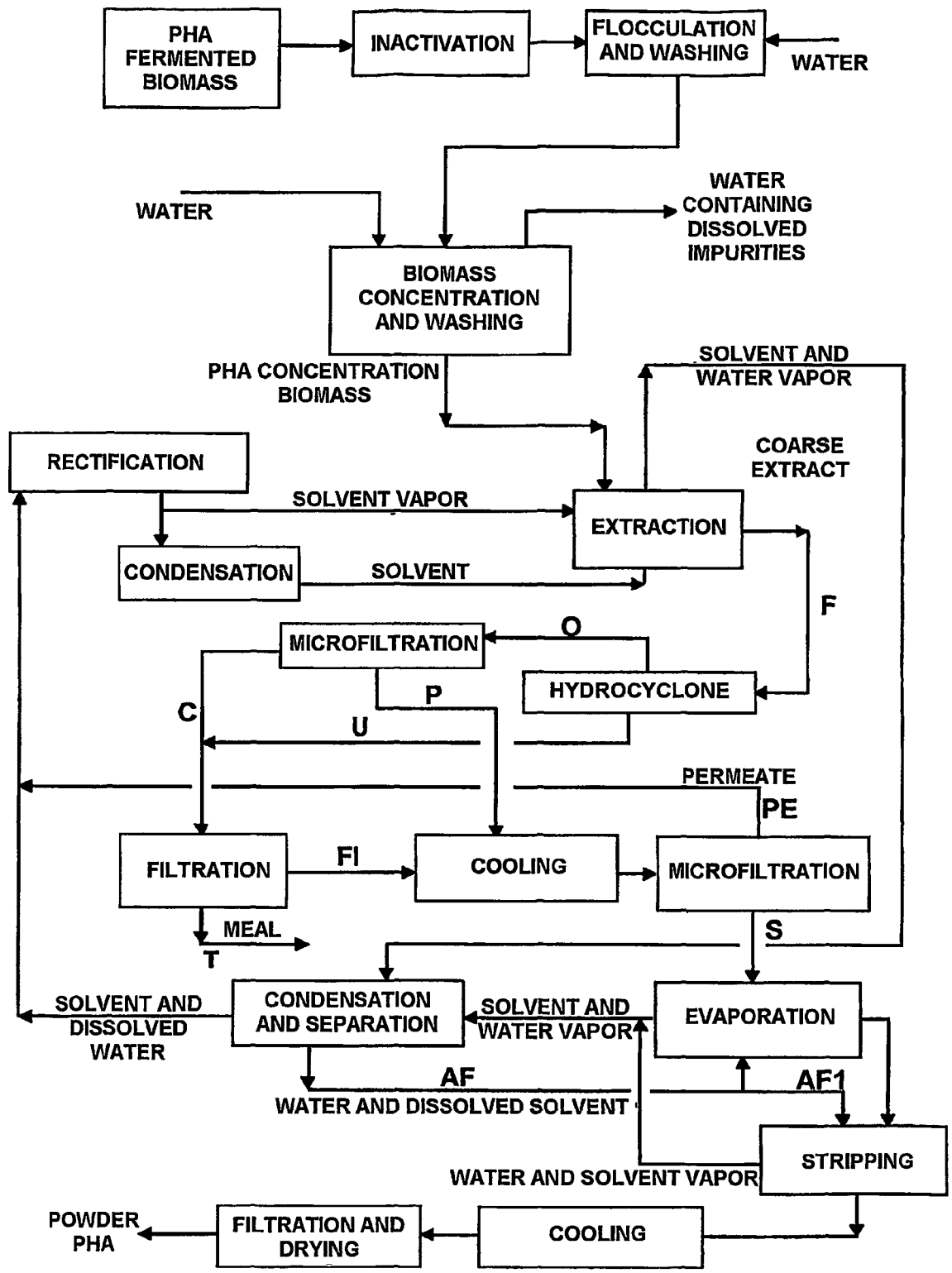

PROCESS FOR RECOVERING POLYHYDROXIALKANOATES ("PHAS") FROM CELLULAR BIOMASS

CROSS REFERENCE TO PRIOR APPLICATION

This is a U.S. national phase application under 35 U.S.C. §371 of International Patent Application No. PCT/BR2004/000237, filed Nov. 25, 2004, and claims benefit of Brazilian Patent Application No. PI 0306230-9, filed Nov. 28, 2003, and Brazilian Patent Application No. PI 0405622-1, filed Nov. 19, 2004, all of which are incorporated by reference herein. The International Application was published in English on Jun. 9, 2005 as WO 2005/052175 A1 under PCT Article 21(2).

FIELD OF THE INVENTION

The present invention refers to a process already proven to be industrially feasible for the extraction and recovery of polyhydroxyalkanoates (PHAs) from a bacterial humid biomass, by employing non-halogenated solvents which are not aggressive to the environment, which process allows obtaining polyhydroxyalkanoates (PHAs) of high purity and high molecular weight by using renewable raw material and energy sources, generally originated from the sugar and alcohol industry using sugarcane.

BACKGROUND OF THE INVENTION

It is presently known in the worldwide industry the need to produce biodegradable and biocompatible materials by using renewable raw materials and energy sources through processes that are not aggressive to the environment.

In the modern society, although the use of plastic materials in a large scale has represented a mark in the history of technological development, the increasing utilization of these materials is leading to a diversity of serious environmental problems. In the case of the industry of petrochemical-derived plastic resins, the annual amounts produced are of about 200 millions tons. These materials, which are very resistant to natural degradation, rapidly accumulate in the disposal areas mainly around the large urban centers. In view of these problems, the development of biodegradable plastic resins has received worldwide attention, mainly those produced by means of a clean technology using renewable sources. Considering the relevance of these facts, the market potential for using these new materials is enormous. The applications of these biodegradable biopolymers with greater chances of success in the market involve products, such as disposable materials, for example packages, cosmetic and toxic agrochemical recipients, medical and pharmaceutical articles, etc.

An important family of the biodegradable biopolymers is the Polyhydroxyalkanoates (PHAs), which are polyesters naturally synthesized by a large number of live beings. With more than 170 representatives described in the literature, the commercial interest in the PHAs is directly related not only to the biodegradability but also to their thermo-mechanical properties and production costs. Thus, only some PHAs have found industrial application, most representatives being the PHB (poly-3-hydroxybutyrate), PHB-V (poly(hydroxybutyrate-co-hydroxyvalerate)), P4HB (poly(4-hydroxybutyrate)), P3HB4HB (poly(3-hydroxybutyrate-co-4-hydroxybutyrate)) and some PHAmcl (polyhydroxyalkanoates of medium chain), the typical representative of this last family being PHHx (polyhydroxyhexanoate).

The chemical structure of the PHAs may be described as a polymeric chain formed by repetitions of the following unit:

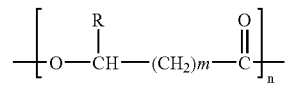

Where R is an alkyl or alkenyl group of variable length and m and n are integers, in the polymers mentioned above R and m assuming the following values:
PHB: R=CH3, m=1
PHB-V: R=CH3 or CH3-CH2-, m=1
P4HB: R=H, m=2
P3HB-4HB: R=H or CH3, m=1 or 2
PHHx: R=CH3-CH2-CH2-, m=1

Most PHAs may be processed in conventional extrusion and injection equipments, without requiring significant modifications for a good processing. It is also possible to process these polymers in cast and coating film systems to be used as packaging materials for the food industry, for example.

As a function of the development stage of these polymers, it is possible to use them to produce packages for personal hygiene products of short use and with low grammage. They can also be used to manufacture containers and packages for agrochemicals, engine oils, disposable diapers, and the like. Moreover, where the intrinsic property of biodegradability is required, the PHAs are applicable according to well defined technical and commercial aspects, such as: garbage bags, golf tees, fishing articles and other products directly connected to the handling of plastic materials in open air.

In agro-industry, the PHAs may be applied to plant pots, reforestation tubes, greenhouse and coverage films and mainly to controlled release system nutrients, fertilizers, herbicides and insecticides.

For biomedical applications, the PHAs can be used for microencapsulating drugs of controlled release, medical sutures and fixation pins for bone fractures, due to their total biocompatibility and to the small reaction from the receiving organism to the presence of a strange body. Furthermore, with a in vivo biodegradation rate which is very slow but continuous and complete, the PHAs present an excellent potential to be applied as a basic structure for re-absorbable prostheses.

The great development of the natural sciences in the last two decades, particularly in biotechnology, has allowed the use of most different natural or genetically modified organisms in the commercial production of PHAs. Particularly relevant for the present invention is the use of determined bacterial strains which are able to produce and to accumulate expressive quantities of these polymers in their interior. Cultivated in specific conditions, which allows reaching high cellular density, high content of intracellular polymer, and yields compatible with the industrial process, these bacterial strains can use different renewable raw materials, such as sugarcane, molasses or hydrolyzed cellulose extracts.

Although attempts have been made for applying the bacterial cells in natura (without using PHA solubilizing agents) as moldable material, such as disclosed in U.S. Pat. No. 3,107,172, the commercial applications of PHAs in most cases require a sufficiently high purity to attain the desired plastic properties. In order to achieve the adequate levels of purity for processing the biopolymer, specially the PHAs, there are normally required steps in which the utilization of solvents for extraction and recovery of the PHA from the residual biomass is indispensable.

In patent EPA-01455233 A2, there are described several possibilities to carry out the digestion of an aqueous suspension of cells containing PHA, using enzymes and/or surfactants to solubilize the non-PHA cellular material. This patent mentions as a possible restriction to the processes that use solvent the fact that they require large quantities of solvents and therefore have high production costs. Nevertheless, it mentions that the solvent step is not eliminated, if a product of high purity is desired. Furthermore, although the enzymes used in this process are added in relative low quantities (1% in relation to the dry cell material) they are very expensive and cannot be recovered in the process, contrarily to what occurs when a solvent is used. Also, high dilution of the cellular material is required, which leads to a high volume of effluents generated in the process.

The usually proposed extraction processes basically consist in exposing the dry or humid cellular biomass containing the biopolymer in a vigorous contact with a solvent that solubilizes it, followed by a step where the cellular residue is separated. The solution containing the biopolymer then receives the addition of an insolubilizing agent, which induces its precipitation in the solvent (see, for example, Brazilian patent PI 9103116-8 filed on Jul. 16, 1991 and published on Feb. 24, 1993.

In the extraction processes through organic solvents often cited in the literature for extraction and recovery of PHA from bacterial biomass, the solvents utilized are partially halogenated hydrocarbons, such as chloroform (U.S. Pat. No. 3,275,610), methylene-ethanol chloride (U.S. Pat. No. 3,044,942), chloroethanes and chloropropanes with boiling point within the range from 65 to 170° C., 1,2-dichloroethane and 1,2,3-trichloropropane (patents EP-0014490 B1 and EP 2446859).

Other halogenated compounds, such as dichloromethane, dichloroethane and dichloropropane are cited in U.S. Pat. No. 4,562,245 (1985), U.S. Pat. No. 4,310,684 (1982), U.S. Pat. No. 4,705,604 (1987) and in European patent 036.699 (1981) and German patent 239.609 (1986).

The processes of extraction and purification of biopolymers from biomass which utilize halogenated solvents are totally prohibitive nowadays, since they are highly aggressive to the environment and to human health. Therefore, a solvent to be used as a potential extractor of the biopolymer from a cellular biomass should first fulfill the condition of not being aggressive to the environment.

In this sense, Brazilian patent PI 9302312-0 (filed on 1993 and granted on Apr. 30, 2002) presents a process of extracting biopolymer from bacterial biomass which employs as solvents high chain alcohols with 3 carbons or the acetates derived therefrom. This patent prefers isoamyl alcohol (3-methyl-1-butanol), amyl acetate (or amyl-acetic ester) and fusel oil, a mixture of high alcohols obtained as a by product of the alcoholic fermentation and which has as main component the isoamyl alcohol. This patent is also characterized for using a single solvent as extractor and purifier, not requiring the utilization of an insolubilizing agent or counter-solvent and/or marginal non-solvent. The precipitation of the solute (biopolymer) of the PHA solution is carried out through the cooling of the solution.

The U.S. Pat. No. 6,043,063 (filed on Apr. 14, 1998 and granted on Mar. 28, 2000), U.S. Pat. No. 6,087,471 (filed on Apr. 14, 1998 and granted on Jun. 11, 2000) and the international patent application WO-98/46783 (filed on Apr. 15, 1997) discloses an extensive list of non-halogenated solvents which could be potentially used as solvents for extracting biopolymer from biomass, but many of them presenting characteristics such as difficult industrial manipulation, toxicity, besides high cost. In said extensive list, which also includes the solvents cited in Brazilian patent PI 9302312-0, only a small number of solvents have potential to be industrially used for extracting biopolymer from vegetal or bacterial biomass, either due to problems regarding incompatibility with the biopolymer, or due to their toxicity, explosiveness, and also high cost. Moreover, Brazilian patent PI 96102256, filed in Brazil on Aug. 16, 1996 and published on Jul. 6, 1999 is even more selective, since it includes compounds that are highly noxious to human health, besides mineral and vegetal oils, carbonic gas (of super critical and expensive extraction technology) among others, as probable solvents useful to extract biopolymer from vegetal or bacterial biomass. At the same time, this patent contemplates the necessity of avoiding solvents that are potentially harmful to health and to the environment.

Since the biopolymers are heat sensitive, i.e. when submitted to temperatures above a determined value, they degrade irreversibly, losing molecular weight, which can definitely affect the properties that characterize them as thermoplastics, it is fundamental to have in mind that the list of solvents with potential to be industrially used becomes even more restrict.

The potential for industrial utilization of the solvent selected to promote the extraction of the biopolymer will be increased if it is associated with an adequate process that allows extracting the biopolymer without causing significant alterations in its molecular weight. Remarkably, in the case of the solvent which needs to be heated above 70° C. to solubilize the biopolymer, the longer it remains exposed to this temperature during the processing, the more it will degrade, which fact can irremediably impair its thermoplastic properties. The lesser alteration the PHA suffers during the process of extraction, the wider will be the range of its possible commercial applications.

As taught in the literature, the kinetics of degradation of the biopolymer, especially the PHA, obeys to a zero-order reaction (see for example the master's degree thesis: Berger, E., 'Elaboration des techniques de separation pour des biopolymeres d'origine bacterienne: les acides poly-β-hydroxyalcanoiques', Departement de Genie Chimique-Ecole Polytechnique—Universite de Montreal, Canada, 1990, pages 72-75). Considering the ratio of degradation of its molecular weight to the time it is exposed at a temperature T as dMW/dt, the equation that defines this degradation is:

$$(dMW/dt)T = k \quad (1)$$

where:
k: is a constant for a given solvent at a given temperature T. thus, if the equation (1) is integrated for a time interval 0-t, we have:

$$MWT = k \cdot t + MWo \quad (2)$$

Where:
MWT: is the molecular weight of the biopolymer after the time of extraction t, for a given temperature T, has elapsed, in a solvent S;
MWo: is the molecular weight of the biopolymer contained in the biomass, at the time t=0, before being submitted to the extraction;
K: is a constant of proportionality for a given temperature T and solvent S.

By way of example, 20 g biomass of dry Alcaligenes eutrophus, containing 70% PHB on a dry base are mixed with 1500 g of isoamyl alcohol (technical grade) at 110° C., submitting the mixture to different times of extraction and filtration for removing insoluble particles from the biomass. The obtained PHB solution is then rapidly cooled to 30° C. to guarantee the precipitation of the PHB, which is subsequently filtrated and dried in air stream at room temperature until the complete depletion of the solvent. Then, the PHB is submitted to molecular weight evaluation by the GPC technique (Gel Permeation Chromatography) to result, after a mathematic adjustment through linear regression, in the following equation of degradation:

$$MWT = -9753.81 \cdot t + 1,000,000, R2 = 0.98 \quad (3)$$

Where:
MWT: is the molecular weight of the polyhydroxybutyrate after the extraction in isoamyl alcohol at 110° C., in Daltons;
T: is the time, in minutes, of exposure of the polyhydroxybutyrate to a temperature of extraction of 110° C. in isoamyl alcohol;
R: is the coefficient of correlation of the experimental points with the equation of adjustment.

Thus, from equation (3) we have that the polyhydroxybutyrate, originally containing a molecular weight of 1,000,000 Da and submitted to an extraction in isoamyl alcohol at 110° C. would give, for a time of 5 minutes, a molecular weight of 951,230 Da; for 15 minutes of exposure, 853,692 Da; for 30 minutes of exposure, 707,410 Da; for 60 minutes, 414,771 Da; and for 90 minutes, 122,230 Da.

Considering that besides the extraction other operations such as evaporation and drying of the solvent are necessary to obtain a pure product with good mechanical properties, and that these operations many times expose the biopolymer to critical situations regarding the material, it is not difficult to imagine the inherent difficulties of processing this type of material. Besides the solvent, it is desirable to have an adequate process which does not degrade the product thermally.

Thus, for purposes of exemplification, the solvents mentioned in U.S. Pat. No. 6,043,063 and their respective temperatures of PHA extraction, at Celsius degrees between parenthesis, are presented in the list below: ethyl butyrate (120° C.), propyl propionate (118° C.), butyl acetate (120° C.), butyl propionate (123° C.), tetrahydrofurfuryl acetate (121° C.), methyl propionate (75° C.), normal-methyl valerate (115° C.), 1-butanol (116° C.), 2-methyl-1-butanol (117° C.), 3-methyl-1-butanol (125° C. and 126° C.), 1-pentanol (125° C. and 126° C.), 3-pentanol (115° C.), amyl alcohol (128° C.), 1-hexanol (134° C.), ethylene glycol diacetate (137° C.), tetrahydrofurfuryl alcohol (117° C.), methyl-amyl-ketone (120° C.), methyl-isobutyl-ketone (115° C.), acetophenone (110° C.), 1,2-diaminopropane (115° C.), alpha-methylstyrene (126° C.), dimethyl sulfoxide (117° C.), propylene carbonate (110° C.), 1,2,3-trimethyl-benzene (121° C.), dimethyl acetamine (90° C.) and dimethylformamide (90° C.). These solvents will have potential to be industrially used only if they are associated with effective processes in which little exposure of the biopolymer to thermal degradation occurs. However, no mention is made to the properties of the materials obtained, especially those referring to the molecular weight of the product.

Other relevant fact regarding the industrial viability of this mode of PHA extraction is that, since it is a process of high energy consumption, we should bear in mind that the viability of the product is also intimately related to the availability of a low cost renewable source of energy.

Considering all the factors mentioned above, in general the properties of biodegradability and sustainability of the PHAs, although they can justify higher prices than those of the traditional polymers of the petrochemical industry, the possibility of the market to assimilate these prices is very limited (Braunegg G, Lefebvre G, Genser F K (1998) Polyhydroxyalkanoates, biopolyesters from renewable resources: Physiological and engineering aspects. J. Biotech. 65: 127-161).

Thus, industrial processes for producing PHAs should contemplate: strains of microorganisms that present high efficiency in the conversion of the raw material into polymer, with a simple and efficient production protocol; raw materials of low cost and high yield; a procedure of extraction and purification of the polymer which allows obtaining a product of high purity, preserving at maximum the original characteristics of the biopolymer, with high yield and efficiency and through processes that are not aggressive to the environment.

Besides these economical aspects, since it is an environmental friendly product, the whole process thereof should be compatible. Thus, the use of environmental harmful products in any production step should be avoided. Moreover, the source of energy used to run the process of production should come from a renewable source. It would not make sense to produce a plastic of low environmental impact if only non-renewable sources of energy are employed. A quite interesting approach to this problem is to have the entire productive chain of the bioplastic incorporated by the agro-industry, in particular by the sugar and alcohol industry (Nonato, R. V., Mantelatto, P. E., Rossell, C. E. V., "Integrated Production of Biodegradable Plastic (PHB), Sugar and Ethanol", Appl. Microbiol. Biotechnol. 57:1-5, 2001).

One of the greatest worldwide successes in the production of alternative fuels is the sugar and alcohol industry in Brazil, which is responsible for about 25% the total amount of alcohol and sugar produced in the planet. While presenting an environmentally negative image in the beginning of the PROÁLCOOL Brazilian program, this type of industry is actually an example of sustainable technology. All energy required to run the production process is generated in loco, by burning the sugar cane bagasses in boilers to produce thermal and electric energy. Moreover, there is an excess of energy that can be used in other incorporated industrial processes.

A renewable and cheap energy allied with the availability of cheap raw materials, such as sugar and molasses and natural solvents obtained as by products of the alcoholic fermentation makes the sugar and alcohol industry the ideal cradle for the production of bioplastics.

Therefore, the present invention encompasses all the characteristics cited above which are necessary to make viable an industrial process for recovering polyhydroxyalkanoates (PHAs), preferably from humid bacterial biomass, using non-halogenated solvents which are not aggressive to the environment, generating a product of high purity and high molecular weight, by employing renewable raw materials and energy sources from the sugar and alcohol industry using sugarcane.

SUMMARY OF THE INVENTION

The present invention is related to a process, already proven to be industrially feasible, for extraction and recovery of polyhydroxyalkanoates (PHAs), from bacterial cellular biomass, obtained through fermentation and in the form of a cellular biomass slurry in aqueous suspension and with a dry cellular material content not inferior to about 18 weight percent of the suspension. In a possible way of carrying out the invention, the concentrated cellular biomass is obtained by submitting the cellular biomass, in suspension in the fermented culture medium, to operations of flocculation and concentration of the biomass cells.

According to the process, the concentrated cellular biomass is initially submitted to a PHA extraction step, which comprises concomitant operations of PHA solvent injection, vigorous agitation and quick heating in the interior of a reactor, in order to form a suspension comprising PHA solvent enriched with dissolved PHA, remaining water from the slurry of the cellular biomass and insoluble residues of the concentrated cellular biomass.

The suspension formed in the reactor is then submitted to a separation, for recovery of the solvent enriched with the dissolved PHA, from the remaining insoluble residues of the cellular biomass.

Then, the PHA solvent solution enriched with PHA is rapidly cooled to a temperature that is sufficient to precipitate substantially all the dissolved PHA.

The present process further comprises the steps of:
cold micro-filtrating the suspension of the PHA precipitated in the PHA solvent containing water and impurities dissolved therein, in order to separate a concentrated paste of precipitated PHA;
submitting the concentrated PHA paste to simultaneous operations of washing with water, heating and agitation, in order to promote the evaporation of part of a certain amount of the solvent, which is adequate to obtain a suspension containing PHA granules provided with high porosity and which are brittle and can be easily sheared, the remaining solvent and water;
submitting the washed and heated PHA granules to agitation and shearing, so as to quickly break them while processing the extraction of the residual solvent by injecting water vapor in the suspension containing the remaining solvent and water, in order to obtain purified PHA particles in the suspension; and
separating the purified PHA particles from the suspension.

From the PHAs found, those with industrial applicability and used in the present invention are: poly-3-hydroxybutirate (PHB), poly(hydroxybutirate-co-hydroxyvalerate) (PHBV), and mixture of these polymers and copolymers.

BRIEF DESCRIPTION OF THE DRAWINGS

The invention will be described below, with reference to the enclosed drawing, given by way of example of a possible way of carrying out the invention, whose single FIG. 1 is a simplified flow chart of said process.

DETAILED DESCRIPTION OF THE INVENTION

A list of definitions of terms used in the description of the present invention is described below:

"alkenyl" means an unsaturated carbonic chain, from C1 to Cn, where n varies from 2 to about 20, which carbonic chain may be linear, branched or cyclic and the unsaturation may be monounsaturated, i.e., with a double or triple bond in the carbonic chain; or polyunsaturated, i.e., with two or more double bonds, or with two or more triple bonds, or still with one or more double bonds and one or more triple bonds in the carbonic chain.

"Alkyl" means a saturated carbonic chain, from C1 to Cn, where n varies from 2 to about 20, which carbonic chain may be straight, branched or cyclic.

"Cellular Biomass" means a biomass coming from any microorganism or plant, which is able to produce PHA naturally or by genetic modification, in order to render it a PHA producer or a high PHA producer.

"Comprises" or "to comprise" means that other steps, or other stages, or other compounds, or other ingredients, which do not affect the end result, may be added or be present. This term may also be substituted for, or substitute the terms: "constituted of", "constituted by", "constituted essentially of" and "constituted essentially by".

"Da" means Dalton, the unit for measuring the molecular weight of polymers.

"To extract polyhydroxyalkanoates from a biomass" or "Extraction of polyhydroxyalkanoates from a biomass" means extracting or the extraction of a determined PHA produced by a biomass that produces a single type of PHA, and additionally it may also mean extracting or the extraction of more than one type of PHA produced by a biomass, for situations in which the PHA producing biomass produces more than only one type of PHA.

"Coarse Extract" means the suspension constituted by the PHA solvent enriched with the PHA extracted from the PHA cellular mass containing, dissolved therein, water and impurities extracted from the cellular mass, and by the insoluble solids, which is the residue of the cellular biomass from which the PHA was extracted.

"Polyhydroxyalkanoates" and "PHA" mean a polymer which encompasses the following repeating unit:

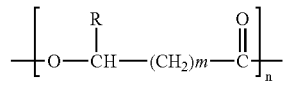

Where R is preferentSially the H or the radical alkyl or the radical alkenyl and m varies from 1 to 4.

"Substantially Atmospheric Pressure" means a pressure very close to the atmospheric, i.e., equal or slightly superior or inferior to the atmospheric pressure.

"Extraction Reactor" means the equipment in which the PHA extraction operation from the PHA producing cellular biomass is processed.

"Rapidly cooling" a stream (solution or suspension) means: to cool this stream (solution or suspension) in some seconds, by expansion, through heat exchange with another cooler stream and/or by cooling by means of heat exchangers.

"Solvent" means a substance capable to dissolve other substance denominated solute, in order to form a mixture denominated solution, of a solute uniformly dispersed in the solvent, regarding molecular size or ionic size.

"PHA Solvent" means a substance capable to dissolve polyhydroxyalkanoates.

"Enriched PHA Solvent" or "enriched PHA solvent solution" means a PHA solvent solution containing the PHA extracted from the PHA producing cellular biomass.

"Virtually free of" or "practically free of" means "to have very small quantity of" or "to have presence of traces of" or "to have a non-significant quantity of" or "to have an almost imperceptible quantity of". The present invention is related to a process, already proven to be industrially feasible, for extraction and recovery of polyhydroxyalkanoates (PHAs), preferably from humid biomass (diluted in water) of microorganisms, using non-halogenated solvents that are not aggressive to the environment, allowing obtaining polyhydroxyalkanoates (PHAs) of high purity and high molecular weight, by employing renewable raw materials and energy sources originated from the sugar and alcohol industry using sugarcane.

There is a relatively large number of publications that describe the PHA extraction by means of non-halogenated solvents from microorganism or vegetal biomass. However, when it is desired to apply the described teachings in a commercial scale, there is a great difficulty in obtaining a product in which the original properties of the intracellular biopolymer are preserved, which characteristics are most of the time fundamental to elaborate commercial products. It is observed that in most of said publications, little attention is given to the thermo-sensitivity of the product at high temperatures. Most non-halogenated solvents considered as candidates to be used in PHA extraction present low solubility to this solute and require high temperatures, normally above 70° C., for PHA extraction and recovery. When it is desired to process the PHA extraction with such solvents in commercial scale, the times necessary for PHA recovery are usually too long, degrading it thermally in an irreversible manner. The product thus obtained, depending on the time of exposure at high temperature, becomes restricted to a very limited number of applications in the industry, or to any other type of application.

The present invention provides a process to be carried out in industrial scale, in which the process steps are combined in such a way as to allow:

a) minimizing the time of exposure of most PHA extracted from the cellular biomass at high temperatures, using non-halogenated solvents, allowing to minimize its degradation, in order to preserve at maximum its original properties, especially its molecular weight;

b) obtaining a product of high purity, normally superior to 99%, preserving the natural color of the biopolymer and with the virtual absence of residual solvent, with no need of including in the process specific additional steps of decolorizing and purifying the produced PHA;

c) obtaining a high level of PHA recovery from the biomass, normally superior to 90%;

d) using, in an integrated manner, renewable raw materials and energy sources originated from the sugar and alcohol industry, thus increasing the profits of the industrial groups that produce sugar and alcohol.

The methods of the present invention can be applied to PHAs produced by natural or genetically modified microorganisms or plants, or to synthetically produced PHAs. PHA is a polymer constituted by repetitions of the following unit:

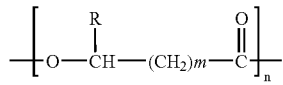

Where R is an alkyl or alkenyl group of variable length and m and n are integers, in the polymers mentioned above R and m assuming the following values:
PHB: R=CH3, m=1
PHB-V: R=CH3 or CH3-CH2-, m=1
P4HB: R=H, m=2
P3HB-4HB: R=H or CH3, m=1 or 2
PHHx: R=CH3-CH2-CH2-, m=1

This invention is applied to PHAs recovered from biomass of microorganisms, preferably to PHB (poly-3-hydroxybutyrate), PHB-V (poly(hydroxybutyrate-co-hydroxyvalerate)), P4HB (poly-4-hydroxybutyrate), P3HB4HB (poly(3-hydroxybutyrate-co-4-hydroxybutyrate)) and some PHAmcl (polyhydroxyalkanoates of medium chain), the typical representative of this last family being the PHHx (polyhydroxyhexanoate).

Process for extracting PHAs by using non-halogenated solvents, with short time of exposure of the biopolymer to a thermal degradation condition.

The present invention refers to a process, illustrated in FIG. 1, which uses a fermented material of bacterial cellular biomass, obtained by fermentation and in the form of a biomass slurry in aqueous suspension and having a dry cellular contents not lower than about 18% by weight.

According to the present invention, the concentrated slurry formed from the cellular biomass can be obtained directly from a fermentation which can reach the necessary minimum concentration of dry material, or by submitting the cellular biomass in suspension in the fermented culture medium to operations of flocculation and concentration of the biomass cells.

In a preferred form of the invention, the cellular biomass in aqueous suspension to be supplied to the process can be further diluted in water, so as to present a water/fermented material mass ratio at maximum of about 3.0:1.0.

In another way of carrying out the invention, the bacterial cellular biomass obtained through fermentation to be processed can be previously thermally deactivated.

In another preferred way of carrying out the invention, the flocculation operation comprises a step of coagulating the cellular biomass effected by acidifying the diluted cellular biomass to a pH from about 1.5 to about 5.5, as well as by adding an alkalizing agent until reaching a pH from about 7 to about 12, the flocculation operation of the biomass cells containing accumulated PHA being effected by adding a flocculating agent. The acidification of the cellular biomass diluted in water can be obtained by adding an acid defined by at least one of the sulfuric and phosphoric acids. The alkalizing agent may comprise calcium hydroxide.

In another preferred way of carrying out the invention, the acidification of the diluted cellular biomass is effected so as to obtain a pH from about 2.0 to about 3.0 and the addition of the alkalizing agent is made so as to adjust the pH of the suspension of the diluted cellular biomass to a range from about 7 to about 12.

The sequential addition of said elements in the flocculation step allows the formation of calcium phosphates, which form bridges with the cell walls of the microorganism containing the PHA, with a resulting positive charge and which are aggregated in a flake through the flocculating agent, leading to the formation of a stable flake presenting a density higher than that of the liquid that involves them.

It should be understood that the step of coagulating the bacterial cellular biomass in suspension in the fermented culture medium could also be carried out by adding only the alkalizing agent, until reaching a pH from 7 to about 12, the flocculation of the cellular biomass containing accumulated PHA being carried out by adding the flocculating agent, as mentioned above.

The formed flakes containing the cells with accumulated PHA are then easily separated from the surrounding fermented liquid culture medium containing the impurities originated from the fermentation, by action of the gravitational force, using for example static decanters or centrifugal force, employing for example in this case centrifuges or decanters.

Where the option is to use centrifuges or decanters, the clarified effluent can be treated again with acid and base, flocculated, submitted to decantation and with the obtained concentrated slurry being sent to the subsequent step together with the other part obtained in the centrifuges or decanters.

Thus, the process allows, in the preferred forms of the invention in which flocculation of the biomass occurs, promoting the partial removal of the extra-cellular impurities dissolved in the fermented culture medium, by separating the flakes therefrom, removing mainly the color elements and other soluble salts which are prejudicial to the subsequent processing steps.

The process further allows the formation of a concentrated biomass slurry containing stable flakes and with a density which is increased in relation to the liquid that involves them.

In another preferred form of the invention, the flocculated cellular biomass is submitted to a process of concentration and washing, resulting in a concentrated biomass slurry in the range of 18-45% (weight/weight), more preferably 25-45%.

The concentrated humid biomass is then submitted to extraction of the intracellular PHA by injecting PHA solvent preferably in the heated liquid form and in the vapor form, under vigorous agitation in a reactor, in order to rapidly provoke heating of the cellular biomass to a temperature between about 90° C. and the boiling temperature of the solvent (at the substantially atmospheric pressure), and to form: a liquid phase comprising PHA solvent enriched with PHA and remaining water of the cellular biomass slurry; a solid phase defined by the insoluble residues of the residual cellular biomass; and a vapor phase containing vapors of water and of the PHA solvents. The water and PHA solvent vapors are condensed and separated in two liquid phases: a rich-solvent phase, which returns to the process in the PHA extracting and recovering phase; and a poor-solvent phase, which is re-circulated in the process to allow for the recovery of the PHA solvent contained therein.

This procedure, besides heating the cellular biomass, also promotes the effect of removing most part of the water supplied with the slurry in the form of a vapor, which is a binary mixture constituted of PHA solvent and water. Then, the vapor phase can be extracted from the reactor to be condensed later, leaving behind a suspension consisting of a solution of PHA solvent enriched with PHA and a small fraction of water dissolved in the solvent, besides insoluble residues of the extracted cellular biomass.

Thus, by way of example, the PHA solvents used can be selected from the group of solvents consisting of: butyl acetate, isobutyl acetate, amyl acetate, isoamyl acetate, isobutyl alcohol, 1-butanol, 1-pentanol (methyl alcohol), 2-methyl-1-butanol, 3-methyl-1-butanol (isoamyl alcohol), 3-pentanol, 1-hexanol, cyclohexanol, propyl propionate, butyl propionate, isobutyl proprionate, ethyl butyrate, isobutyl isobutyrate, and mixtures thereof. Preferably, the solvent can be isoamyl alcohol, or isomeric mixtures of isoamyl alcohol, and more preferably isoamyl alcohol can be obtained from fractionation of the fusel oil as a by-product of the ethanol fermentation, the fusel oil primarily consisting of isoamyl alcohol and isomers thereof, besides impurities, such as: ethanol, n-propanol, isobutanol, n-butanol and water.

The contact between the extracting solvent and the PHA cellular biomass is promoted in controlled conditions and by an agitation system which is dimensioned to allow a vigorous contact between the parts, and to guarantee an insoluble biomass residue with uniform particle size, which facilitates the subsequent operations.

As illustrated in FIG. 1, the obtained stream, herein denominated stream F and consisting of the suspension containing PHA and water dissolved in the solvent and by biomass insoluble residues, in a preferred form of the invention is then fed to a centrifugal separating element, for example a hydrocyclone, in which the application of a centrifugal force of low intensity (some times the gravitational force) leads to the generation of two streams: one stream consisting of a suspension with low concentration of residual insoluble solids of biomass in a solution containing PHA and a small fraction of water dissolved in the PHA solvent, herein denominated stream O, and the other stream containing a suspension with concentrated biomass insoluble residues in a solution containing PHA and a small fraction of dissolved water, herein denominated stream U. The separation of the two streams flowing from the centrifugal separating element is made so that the stream U is of about 15-35% (weight/weight) of the stream F and contains about 55-75% (weight/weight) of the solids originally present in the stream F and further containing a fraction of intracellular PHA to be recovered. The separation of these two streams as described herein and carried out under effect of a centrifugal force of low intensity in static, strong and low cost equipments such as the hydrocyclones for example, dispenses the use of high cost mechanical centrifuges which would require the use of inert gas atmospheres, as a function of the limits of explosibility and inflammability of the PHA solvents.

Such separation is assured herein by the higher density of the particles of residual insoluble solids in relation to the solvent involving them, which is imparted by the initial coagulation in which heavy particles, such as those of calcium phosphate, are bonded to the cells containing intracellular PHA and constituents of the cellular biomass. Another important effect is the capacity of the extraction system to yield particles with a uniform granulometric distribution during the extraction, which assures high efficiency of separation and concentration of the solids containing non-extracted intracellular PHA, upon the utilization of a centrifugal separating element of low intensity.

Optionally, the stream O can be submitted to a process of membrane micro-filtration or of filtration in precoat filters, in which two streams are generated: one stream P, which is permeated through the membrane, and a stream C of membrane concentrate. The stream P which is about 50%-90% (weight/weight) of the stream O is free of insoluble solids and contains PHA, water and small fractions of ashes and color compounds dissolved in the PHA solvent, being immediately cooled to a temperature of about 45° C. or lower. The stream C which is about 10-50% the stream O, is concentrated in relation to the concentration of residual solids of the extracted biomass about 2-10 times the original content of these solids in the stream O and it contains a fraction of PHA, water, ashes and color compounds dissolved in the PHA solvent.

Optionally, the stream U and the stream C, which are concentrated in insoluble residues of extracted biomass and poor in PHA, can be joined and sent to a process of recovery of the remaining PHA dissolved in the PHA solvent, by means of a process of separation, for example by filtration, in which a filtrated stream (denominated F1) is generated containing PHA, water, ashes, color compounds, dissolved in the PHA solvent, and an end meal, herein denominated T, containing the residual insoluble solids of the extracted biomass.

Optionally, the stream U and the stream C, which are concentrated in insoluble residues of extracted biomass and poor in PHA, can be joined and sent to a process of recovery of the remaining PHA dissolved in the PHA solvent, by means of a process of separation, for example by filtration, in which a filtrated stream (denominated F1) is generated containing PHA, water, ashes, color compounds, dissolved in the PHA solvent, and an end meal, herein denominated T, containing the residual insoluble solids of the extracted biomass. Optionally, the stream U, the stream C and a new quantity of PHA solvent in the liquid and in the vapor form can be mixed again in adequate agitation conditions, thus forming a new stream which will be submitted again to the previously described process. Thus, the resulting end effluent, concentrated in insoluble residues of extracted cellular biomass and poor in PHA, is finally submitted to a recovery process of the remaining PHA, dissolved in the PHA solvent, by a separation process, for example by filtration. The described extraction process comprises a number of steps such that it allows the recovery of quantities higher than about 95% (weight/weight) of the PHA originally contained in the biomass, with retention times shorter than about 10-20 minutes, in order to obtain a PHA presenting a molecular weight at minimum of about 850,000 Da from a biomass slurry containing PHA with a molecular weight at minimum of about 1,000,000 Da.

Still optionally, the stream O which contains the insoluble solids remaining from the process effected in the centrifugal separating element (for example, a hydrocyclone), can be sent to a process for separating the insoluble solids, without being submitted to a membrane micro-filtration process, thus obtaining a filtrate stream containing PHA dissolved in the solvent and free of any insoluble solids of the biomass and leaving behind a meal containing said insoluble impurities. The PHA thus recovered has a molecular weight slightly lower than that obtained by membrane micro-filtration.

In the preferred form of the invention, the coarse extract stream F containing the insoluble residues of extracted biomass can be also sent directly to the recovery process of the PHA dissolved in the PHA solvent, without passing through the centrifugal separating element and the membrane micro-filtration; in this case, in relation to the previous option, the PHA presents a similar quality, but a molecular weight which is slightly reduced due to the longer retention time of the polymer resulting from the separation process of the insoluble solids.

The stream P and the stream FI described above, freed of insoluble residues of cellular biomass and containing PHA, water, ashes and some color compounds dissolved in PHA solvent, upon being rapidly cooled to temperatures around 45° C. or lower, cause PHA precipitation, forming a suspension whose molecular weight is at minimum of about 850,000 Da, starting from a biomass slurry containing PHA with a molecular weight at minimum of about 1,000,000 Da. This precipitation can be further aided by the introduction of a crystallization germ.

The PHA suspension in a PHA solvent obtained through precipitation by cooling, containing dissolved therein water, ashes and dissolved color compounds, is then submitted to a separation process, preferably by micro-porous polymeric membranes. This process allows obtaining a permeate stream PE, which is about 60%-90% the mass flow fed to the membrane, comprising PHA solvent, water, soluble ashes and color compounds dissolved in the PHA solvent and virtually free of PHA; and another stream, of about 40%-10% the fed stream, which consists of a concentrated PHA suspension and a fraction of ashes and color compounds dissolved in the PHA solvent. This step, such as described in this invention, besides allowing to concentrate the PHA suspension to a concentration up to about 3.5-8% (weight/weight) in conditions that are highly favorable to the preservation of the PHA molecular weight and in a process employing a temperature that is close to the ambient temperature and through physical means (membranes), further leads to the simultaneous elimination, by means of the permeate, of about 70%-90% the impurities dissolved, which were constituents of the PHA suspension.

The suspension previously concentrated with PHA, with a PHA concentration ranging from 3.5%-8% (weight/weight) (and defined by the stream S in FIG. 1, is then submitted to a concentration step by means of evaporation, at atmospheric pressure, and preferentially in multiple vacuum effects, in which are simultaneously fed the PHA suspension and a weak water stream AF, recovered in the process and containing PHA solvent dissolved therein. This weak water is fed in the evaporators in a proportion such as to allow obtaining a suspension basically containing PHA, PHA solvent and water, forming agglomerates of PHA granules presenting high porosity, in a brittle agglomeration and which can be easily sheared. This suspension is then simultaneously with the evaporation submitted to a comminution process in an mechanical shearing element, for example a circulation centrifugal pump, in which the agglomerates of PHA granules, with high porosity and brittle, are rapidly and adequately ruptured, in order to obtain a suspension of much finer PHA particles, which can be abundantly washed during the evaporation process of the PHA solvent. This suspension, to which is added a weak water stream (AF1), is then submitted to evaporation of the end residual solvent (stripping), until it is completely extracted from the remaining liquid (mother liquor), upon injecting live steam simultaneously with the re-circulation of the suspension obtained in the prior step. By repeating the shearing process during the evaporation, it is possible to obtain a controlled comminution of the PHA until it becomes a powder in suspension in the remaining liquid free of solvent. Thus, at the end of the process, a suspension of PHA particles is obtained, finely dispersed in the remaining liquid (mother liquor), which in turn contains dissolved therein the impurities removed from the PHA. This suspension is then rapidly cooled to about 45° C. or less and submitted to a process of separating the solids from the liquids, for example by filtration, and rinsing the filtrated cake with fresh water, containing the PHA particles.

Thus, these final steps of evaporation, stripping, cooling and filtration allow, at the same time in which the evaporation is being carried out, to effect the depletion of the PHA solvent from the medium and the final purification of the PHA particles without damages to the PHA molecular weight. Furthermore, it allows obtaining particles with a granulometric distribution, which is adequate to the drying process, in the range of 40-400 µm, and preferably about 100-200 µm, in order to allow the use of mild drying conditions, i.e., the PHA submitted to moderate temperatures and short retention time. The PHA biopolymer obtained after the drying step presents high level of purity, extremely low levels of residual solvent, color, ashes and impurity, and a high global yield, i.e. a quantity of recovered PHA in relation to the PHA contained in the original biomass higher than about 90% (weight/weight).

EXAMPLES

Example 1.1

Inactivation of the Fermented Biomass 10 m3 of a suspension of fermented biomass of Alcaligenes eutrophus, containing 150 g/l of total dry material, formed by bacterial cells containing about 60-75% PHB by weight, are passed through a regenerative heat exchanger TCR1 at a flowrate of 4 m3/h, subsequently receiving direct injection of vapor, in order to increase the temperature to 85° C. This suspension is conducted to a retention vessel with useful volume of 1 m3 and pumped back to the exchanger TCR-1, where it is cooled by the biomass suspension, which enters in the process and is in turn heated. The biomass suspension, which leaves the process at about 45° C., maintains practically unaltered the concentrations of dry material and PHB. However, the bacterial cells have now their enzymatic system inactivated, and are therefore unable to degrade the accumulated PHB. This suspension is then conducted to the coagulation and decantation process.

Example 1.2

Wash and Concentration of Fermented Biomass

To 5 m3 of previously inactivated PHB fermented biomass of Alcaligenes eutrophus, 5 m3 of water under mild agitation, and then phosphoric acid are added, until reaching pH of 2.8-3.5, and milk of lime until reaching pH 7.0-8.0. The coagulated biomass suspension then receives the addition of 10-20 ppm of an anionic polyelectrolyte, being slowly agitated and then maintained under rest for decantation. The supernatant is then removed, leaving a biomass slurry with about 10-12% dry material. The obtained slurry is then fed to a centrifuge decanter at a flowrate of about 1200 kg/h and then it further receives the addition of polyelectrolyte, in a sufficient quantity to flocculate, and water in a proportion of about 20% (weight/weight) of the fed slurry flowrate. The clarified material is then removed, generating about 2400 kg of slurry with about 20-25% solids from which 70-75% correspond to PHB.

Example 1.3.1

PHB Extraction and Recovery Using Isoamyl Alcohol as Solvent in a One-Stage Extraction The Alcaligenes eutrophus biomass concentrated at 25% dry material and containing about 60-75% PHB with molecular weight of 1,000,000 Da is fed to a mechanically agitated reactor, maintained at about 105° C. at a flowrate of 350-450 kg/h, in which it receives the addition of 7290 kg/h of isoamyl alcohol heated at about 105° C. and vapor of isoamyl alcohol at 135° C., in a sufficient quantity to evaporate the excess of water contained in the slurry, generating a stream of about 1250 kg/h of vapor composed of about 15% water and 85% isoamyl alcohol, and another stream denominated coarse extract of about 8000 kg/h of a suspension containing PHB (molecular weight of about 900,000 Da) and water dissolved in the isoamyl alcohol, and insoluble residues of extracted biomass. The coarse extract is then continuously fed to a hydrocyclone, where the flow is separated in two streams: one stream of about 75% the feeding flowrate in the upper portion and containing about 65% the insoluble solids originally contained in the fed coarse extract; and another stream in the lower portion of about 25% the fed flow and containing 75% the insoluble solids originally contained therein. The upper stream of the hydrocyclone, poor in insoluble solids, is then fed to an unit of membrane micro-filtration at a flowrate of 6000 kg/h, generating a stream of about 1500 kg/h (¼) concentrated in residual insoluble solids of the extracted biomass, and a permeate stream of 4500 kg/h (¾) free of residual insoluble solids of the extracted biomass and enriched with PHB with molecular weight within the range of 800,000-880,000 Da. The retention time in the process is of about 3-10 minutes. The stream rich in insoluble solids of the hydrocyclone (lower phase) and of the membrane are then mixed and sent to a filtration step for example in a plate filter, at a flowrate of 2000 kg/h, generating a stream of about 1800 kg/h, which is a PHB solution free of insoluble solids in suspension enriched with PHB with a molecular weight between 580,000 and 780,000 Da, and a meal containing the insoluble solids of the extracted biomass of about 200 kg/h. The PHB recovery of the process is higher than 95% (weight/weight) in relation to the fed PHB of the biomass, i.e., 50-80 kg of PHB/h, depending on the biomass flow and purity. Both the filtrates obtained in the membrane and filter extraction process are rapidly cooled to a temperature equal to or lower than about 45° C., in order to guarantee the precipitation of PHB in the solvent. The PHB precipitated in isoamyl alcohol coming from the membrane micro-filtration has molecular weight in the range between 800,000 and 870,000 Da and from the conventional filtration in the range between 580,000 and 780,000 Da.

Optionally, the stream of coarse extract of about 8000 kg/h of a suspension containing PHB (molecular weight about 900,000 Da) and water dissolved in the isoamyl alcohol and insoluble residues of extracted biomass is directly sent to the filtration step, for example in plate filters, in which two streams are obtained: a filtrate stream of about 7800 kg/h which is a PHB solution free of insoluble solids in suspension enriched with PHB with a molecular weight between 580,000 and 780,000 Da; and a meal containing the insoluble solids of the extracted biomass of about 200 kg/h. The filtrate obtained in the process is then rapidly cooled to a temperature equal or inferior to about 45° C., in order to guarantee the precipitation of PHB in the solvent. The PHB precipitated in isoamyl alcohol has a molecular weight in the range of 80,000-780,000 Da.

The PHB recovery of the process is higher than 95% (weight/weight) in relation to the fed PHB of the biomass, i.e. 50-80 kg of PHB/h, depending on the biomass flow and purity.

Example 1.3.2

PHB Extraction and Recovery Using Isoamyl Alcohol as Solvent in a Three-Stage Extraction In an arrangement of three reactors in series, the Alcaligenes eutrophus biomass concentrated up to 25% dry material and containing about 60-75% PHB with a molecular weight of about 1,000,000 Da, is fed to the first mechanically agitated reactor, maintained at about 105° C. and at a flowrate of 350-450 kg/h. In the third reactor isoamyl alcohol is fed at a flowrate of 7290 kg/h heated at about 105° C. Isoamyl alcohol vapor at 135° C. is fed to the three extraction stages in a sufficient quantity to guarantee the evaporation of the excess of water contained in the slurry. This procedure conducts to the generation of a water vapor and isoamyl alcohol total stream of about 1250 kg/h, comprising respectively 15% water and 85% isoamyl alcohol, and another stream, flowing from the first extraction stage and denominated coarse extract, of about 8000 kg/h of a suspension containing PHB and water dissolved in the isoamyl alcohol and insoluble residues of extracted biomass. The coarse extract coming from the first stage is then continuously fed to the hydrocyclone 1, where the flow is separated in two streams: a top stream, comprising about 75% the feeding flow and containing about 40%-45% the insoluble solids originally contained in the fed coarse extract; and a bottom stream (in the lower portion) of about 25% the fed flow and containing about 55%-60% the insoluble solids originally contained therein and which is conducted to the next stage (2). The top stream of the hydrocyclone 1 poor in insoluble solids is then fed to a membrane micro-filtration unit at a flowrate of 6000 kg/h, generating a stream of about 2000 kg/h (⅓) concentrated in residual insoluble solids of the extracted biomass, and a permeate stream of 4000 kg/h (⅔) free of residual insoluble solids of the extracted biomass. The bottom stream of the hydrocyclone 1 is conducted to the second extraction stage where it receives the top stream of the hydrocyclone 3 and the stream concentrated in insoluble solids generated in the membrane micro-filtration. The bottom stream of the hydrocyclone 3 containing about 55-65% the insoluble solids of the extracted biomass is then sent to a filtration step, for example in plate filters at a flowrate of 2000 kg/h, generating a stream of about 1800 kg/h which is a PHB solution free of insoluble solids in suspension, and a meal containing the insoluble solids of the extracted biomass of about 200 kg/h. The PHB recovery of the process is higher than 98% (weight/weight) in relation to the fed PHB of the biomass, i.e., 51-82 kg of PHB/h. Both the filtrates obtained in the membrane and filter extraction process are rapidly cooled to a temperature which is equal to or lower than about 45° C., in order to guarantee the precipitation of PHB in the solvent, isoamyl alcohol.

Optionally, the top stream of the hydrocyclone 1 of about 6000 kg/h poor in insoluble solids is then directly sent to the filtration step, for example in plate filters, where two streams are obtained: a filtrate stream of about 5800 kg/h, which is a PHB solution free of insoluble solids in a suspension enriched with PHB with a molecular weight within the range of 650,000-780,000 Da; and a meal containing the insoluble solids of the extracted biomass of about 200 kg/h. The filtrate obtained in the process is then rapidly cooled to a temperature equal to or lower than about 45° C., in order to guarantee the precipitation of PHB in the solvent. The PHB precipitated in isoamyl alcohol has molecular weight in the range of 650,000-780,000 Da.

The PHB recovery of the process is higher than 95% (weight/weight) in relation to the fed PHB of the biomass, i.e., 50-80 kg of PHB/h, depending on the biomass flow and purity.

Example 1.3.3

PHB Extraction and Recovery Using Isoamyl Acetate as Solvent

Test of PHB Solubility in Isoamyl Acetate:

To a 500 ml round bottom distillation flask, 31 g of concentrated biomass of Alcaligenes eutrophus, containing 28.11% dry material and 16.09% PHB with molecular weight of 1,000,000 Da, and 250 g of isoamyl acetate were added. The suspension was then submitted, under agitation, to evaporation of the solvent and water, by using a heating blanket coupled to the distillation flask. The thus generated binary vapor was conducted to a straight tube condenser (Liebig type) for condensation and the resulting condensate was collected in an Erlenmeyer recipient. The suspension was maintained in an evaporation process under agitation until reaching the extraction temperature. The temperature was read in a mercury thermometer affixed to one of the flask nozzles and maintained in contact with the vapor phase inside the flask. The extraction temperature was reached after an evaporation time of about 14 minutes had elapsed, the boiling temperature of the mixture passing from about 104° C. (initial temperature) to about 123° C. (extraction temperature), in this period being generated about 34 ml of condensate consisting of about 70% (v/v) isoamyl acetate and the remaining volume being the water coming from the concentrated biomass. The suspension was then maintained in a condensate reflux regime under agitation for about 10 minutes at the temperature of 123° C. (extraction temperature) and then still heated being filtrated in a filter paper for separating the insoluble part from the part dissolved in the filtrated solvent. The hot filtrated material containing about 0.90% (w/w) solubilized PHB was then cooled for PHB precipitation, was concentrated through filtration, submitted to evaporation of the solvent and afterwards to drying. The obtained PHB presented a molecular weight of about 495,000 Da. The quantity of concentrated biomass used in the tests was about 2.0-3.5 times greater than the quantity needed to reach the concentration of PHB saturation in the solvent at the extraction temperature employed. Thus, the concentration of the solute (PHB) saturation in the solvent (isoamyl acetate) for the employed extraction temperature could be determined.

Test of PHB Extraction in Isoamyl Acetate:

To a 500 ml round bottom distillation flask, 10 g of concentrated biomass of Alcaligenes eutrophus containing 28.11% dry material and 16.09% PHB with molecular weight of about 1,000,000 Da and 200 g of isoamyl acetate were added. The suspension was then submitted to evaporation of the solvent and water, by using a heating blanket coupled to the distillation flask, the thus generated binary vapor being conducted to a straight tube condenser (Liebig type) for condensation and the resulting condensate collected in an Erlenmeyer recipient. The suspension was maintained in evaporation process under agitation until reaching the extraction temperature. The temperature was read in a mercury thermometer affixed to one of the flask nozzles and maintained in contact with the vapor phase inside the flask. The suspension was then maintained in a condensate reflux regime under agitation for about 10 minutes at the temperature of 123° C. (extraction temperature). The thus obtained material was then submitted to a heat decantation process and the insoluble solid residue resulting from the extraction could be separated from the PHB solubilized in the solvent. The solution containing dissolved PHB was cooled for precipitation of PHB and the PHB mass extracted in this stage was measured. The solid residue obtained in the first stage received a new addition of 200 g of isoamyl acetate and was again submitted to extraction for 10 minutes. The other procedures were repeated until totalizing three extraction stages. About 41% the PHB originally contained in the cellular biomass was extracted in the first stage, 13% in the second stage and 8% in the third stage. The PHB thus obtained remained in the range of 730,000 Da-750,000 Da.

Example of Extrapolation to Industrial Scale

The Alcaligenes eutrophus biomass concentrated at 28.11% dry material and containing 16.09% PHB with molecular weight of about 1,000,000 Da is fed to a mechanically agitated reactor maintained at about 123° C. at a flowrate of 500 kg/h, in which it receives the addition of 9,521 kg/h of isoamyl acetate heated at about 123° C., in the liquid and in the vapor form, in a sufficient quantity to evaporate the excess of water contained in the slurry, generating a stream of about 833 kg/h of vapor composed of about 30% (v/v) water and 70% (v/v) isoamyl acetate, and another stream denominated coarse extract of about 8,969 kg/h of a suspension containing PHB and water dissolved in the isoamyl acetate and insoluble residues of extracted biomass. The coarse extract is then continuously fed to a hydrocyclone, where the flow is separated in two streams: one stream of about 75% the feeding flow in the upper part and containing about 35% the insoluble solids originally contained in the fed coarse extract; and another stream in the lower part of about 25% the fed flow and containing about 65% the insoluble solids originally contained therein. The upper stream of the hydrocyclone, poor in insoluble solids, is then fed to a membrane micro-filtration unit at a flowrate of 6,891 kg/h, generating a stream of about 1,149 kg/h (⅙) concentrated in residual insoluble solids of the extracted biomass, and a permeate stream of 5,743 kg/h (⅚) free of residual insoluble solids of the extracted biomass.

The retention time in the process is of about 10 minutes. The stream rich in insoluble solids from the hydrocyclone (lower phase) and from the membrane are then mixed and sent to a filtration step, for example in plate filters, at a flowrate of 3,446 kg/h, generating a stream of about 3,294 kg/h which is a PHB solution free of insoluble solids in suspension and a meal containing the insoluble solids of the extracted biomass of about 151.5 kg/h. The PHB recovery of the process is higher than 95% (weight/weight) in relation to the fed PHB of the biomass, i.e., 70-80 kg of PHB/h, depending on the biomass flow and purity. Both the filtrates obtained in the membrane and filter extraction process are rapidly cooled to a temperature equal to or lower than about 45° C., in order to guarantee the precipitation of PHB in the solvent.

Example 1.3.4

PHB Extraction and Recovery Using Butyl Acetate as Solvent

Test of PHB Solubility in Butyl Acetate:

31 g of concentrated biomass of Alcaligenes eutrophus containing 28.11% dry material and 16.09% PHB with molecular weight of 1,000,000 Da and 250 g of butyl acetate were added to a 500 ml round bottom distillation flask. The suspension was then submitted, under vigorous agitation, to evaporation of the solvent and water by using a heating blanket coupled to the distillation flask, the thus generated binary vapor being sent to a straight tube condenser (Liebig type) for condensation and the resulting condensate collected in an Erlenmeyer recipient. The suspension was maintained in evaporation process under agitation until reaching the extraction temperature. The temperature was read in a mercury thermometer affixed to one of the flask nozzles and maintained in contact with the vapor phase inside the flask. The extraction temperature was reached after an evaporation time of about 28 minutes had elapsed, the boiling temperature of the mixture passing from about 91.5° C. (initial temperature) to about 121.5° C. (extraction temperature), in this period being generated about 131 ml of condensate consisting of about 83% (v/v) isoamyl acetate and the remaining volume being the water coming from the concentrated biomass. The suspension was then maintained in a condensate reflux regime under agitation for about 10 minutes at the temperature of 121.5° C. (extraction temperature), being then filtrated, still heated, in filter paper, for separating the insoluble part from the part dissolved in the filtrated solvent. The heated filtrated material, containing about 0.98% (w/w) of solubilized PHB, was then cooled for precipitation of the PHB, concentrated through filtration, submitted to evaporation of the solvent and afterwards to drying. The obtained PHB presented a molecular weight of about 502,000 Da. The quantity of concentrated biomass employed in the tests was about 2.0-3.5 times greater than the quantity necessary to reach the concentration of PHB saturation in the solvent, at the employed extraction temperature. Thus, the concentration of saturation of the solute (PHB) in the solvent (isoamyl acetate) for the employed extraction temperature could be determined.

Test of PHB Extraction in Butyl Acetate:

10 g of concentrated biomass of Alcaligenes eutrophus containing 28.11% dry material and 16.09% PHB with molecular weight of 1,000,000 Da and 200 g of butyl acetate were added to a 500 ml round bottom distillation flask. The suspension was then submitted to evaporation of the solvent and water, by using a heating blanket coupled to the distillation flask, the thus generated binary vapor being conducted to a straight tube condenser (Liebig type) for condensation and the resulting condensate collected in an Erlenmeyer recipient. The suspension was maintained in evaporation process under agitation until reaching the extraction temperature. The temperature was read in a mercury thermometer affixed to one of the flask nozzles and maintained in contact with the vapor phase inside the flask. The suspension was then maintained in a condensate reflux regime under agitation for about 10 minutes at the temperature of 121.5° C. (extraction temperature). The thus obtained material was then submitted to a heat decantation process and the insoluble solid residue resulting from the extraction was separated from the PHB solubilized in the solvent. The solution containing dissolved PHB was cooled for precipitation of PHB and the PHB mass extracted in this phase was measured. The solid residue obtained in the first stage received a new addition of 200 g of butyl acetate and was again submitted to extraction for 10 minutes. The other procedures were repeated until totalizing three extraction stages. About 62.5% the PHB originally contained in the cellular biomass was extracted in the first stage, 18.5% in the second stage and 7.0% in the third stage. The molecular weight of the obtained PHB remained in the range of 740,000 Da-780,000 Da.

Example of Extrapolation to Industrial Scale

The Alcaligenes eutrophus biomass concentrated at 28.11% dry material and containing about 16.09% PHB with a molecular weight of about 1,000,000 Da is fed to a mechanically agitated reactor maintained at about 121.5° C. at a flowrate of 500 hg/h, in which it receives the addition of 9,577 kg/h of butyl acetate heated at about 121.5° C., in the liquid and in the vapor form, in a quantity sufficient to evaporate the excess of water contained in the slurry, generating a stream of about 1732 kg/h of vapor consisting of about 17% water and 83% butyl acetate, and another stream, denominated coarse extract, of about 8,175 kg/h of a suspension containing PHB and water dissolved in the butyl acetate and insoluble residues of the extracted biomass. The coarse extract is then continuously fed to a hydrocyclone, where the flow is separated in two streams: one stream of about 75% the feeding flow in the upper part and containing about 35% the insoluble solids originally contained in the fed coarse extract; and another stream in the lower part of about 25% the fed flow and containing about 65% the insoluble solids originally contained therein. The upper stream of the hydrocyclone, poor in insoluble solids, is then fed to a membrane microfiltration unit, at a flowrate of 6,258 kg/h, generating a stream of about 1,043 kg/h (⅙) concentrated in residual insoluble solids of the extracted biomass, and a permeate stream of 5,215 kg/h (⅚) free of residual insoluble solids of the extracted biomass. The retention time in the process is of about 10 minutes. The stream rich in insoluble solids of the hydrocyclone (lower phase) and of the membrane are then mixed and sent to a filtration step, for example in plate filters, at a flowrate of 3,129 kg/h generating a stream of about 2,978 kg/h, which is a PHA solution free of insoluble solids in suspension, and a meal containing the insoluble solids of the extracted biomass of about 151.5 kg/h. The PHBV recovery of the process is higher than 95% (weight/weight) in relation to the fed PHBV of the biomass, i.e., 70-80 kg of PHBV/h, depending on the biomass flow and purity. Both the filtrates obtained in the membrane and filter extraction process are rapidly cooled to a temperature which is equal or inferior to about 45° C., in order to guarantee the precipitation of PHBV in the solvent.

Example 1.3.5

PHB Extraction and Recovery Using Propyl Propionate as Solvent

Test of PHB Solubility in Propyl Propionate:

To a 500 ml round bottom distillation flask, 31 g of concentrated biomass of Alcaligenes eutrophus, containing 28.11% dry material and 16.09% PHB and with a molecular weight of 1,000,000 Da and 250 g of propyl propionate were added. The suspension was then submitted, under vigorous agitation, to evaporation of the solvent and water, by using a heating blanket coupled to the distillation flask, the thus generated binary vapor being conducted to a straight tube condenser (Liebig type) for condensation and the resulting condensate collected in an Erlenmeyer recipient. The suspension was maintained in evaporation process under vigorous agitation until reaching the extraction temperature. The temperature was read in a mercury thermometer affixed to one of the flask nozzles and maintained in contact with the vapor phase inside the flask. The extraction temperature was reached after an evaporation time of about 15 minutes had elapsed, the boiling temperature of the mixture passing from about 92° C. (initial temperature) to about 113° C. (extraction temperature), in this period being generated about 100 ml of condensate, consisting of about 80% (v/v) propyl propionate and the remaining volume being the water coming from the concentrated biomass. The suspension was then maintained in a condensate reflux regime under vigorous agitation for about 10 minutes, at the temperature of 113° C. (extraction temperature), being subsequently filtrated, still heated, in filter paper, for separating the insoluble part from the part dissolved in the filtrated solvent. The heated filtrated material containing about 1.24% (p/p) of solubilized PHB was then cooled for precipitation of the PHB, was concentrated through filtration, submitted to evaporation of the solvent and afterwards to drying. The obtained PHB presented a molecular weight of about 430,000 DA. The quantity of concentrated biomass used in the tests was from about 2.0-3.5 times greater than the necessary quantity to reach the concentration of PHB saturation in the solvent, at the employed extraction temperature. Thus, the concentration of saturation of the solute (PHB) in the solvent (propyl propionate) for the employed extraction temperature could be determined.

Test of PHB Extraction in Propyl Propionate:

To a 500 ml round bottom distillation flask, 10 g of concentrated biomass of Alcaligenes eutrophus containing 28.11% dry material and 16.09% PHB with a molecular weight of 1,000,000 Da and 200 g of propyl propionate were added. The suspension was then submitted to evaporation of the solvent and water, by using a heating blanket coupled to the distillation flask, the thus generated binary vapor being conducted to a straight tube condenser (Liebig type) for condensation and the resulting condensate collected in an Erlenmeyer recipient. The suspension was maintained in evaporation process under agitation until reaching the extraction temperature. The temperature was read in a mercury thermometer affixed to one of the flask nozzles and maintained in contact with the vapor phase inside the flask. The suspension was then maintained in a condensate reflux regime under agitation for about 10 minutes, at the temperature of 113° C. (extraction temperature). The material thus obtained was then submitted to a heat decantation process and the insoluble solid residue resulting from the extraction was separated from the PHB solubilized in the solvent. The solution containing dissolved PHB was cooled for precipitation of PHB and the PHB mass extracted in this stage was measured. The solid residue obtained in the first stage received a new addition of 200 g of propyl propionate and was again submitted to extraction during 10 minutes. The other procedures were repeated until totalizing three extraction stages. About 62.0% the PHB originally contained in the cellular biomass was extracted in the first stage, 18.5% in the second stage and 6.0% in the third stage. The molecular weight of the obtained PHB was about 730,000 Da.

Example of Extrapolation to Industrial Scale

The Alcaligenes eutrophus biomass concentrated at 28.11% dry material and containing about 16.09% PHB with a molecular weight of about 1,000,000 Da is fed to a mechanically agitated reactor maintained at about 113° C. at a flowrate of 500 kg/h, in which it receives the addition of 7,406 kg/h of butyl acetate heated at about 113° C., in the liquid and in the vapor form, in a sufficient quantity to evaporate the excess of water contained in the slurry, generating a stream of about 1,156 kg/h of vapor composed of about 20% water and 80% (v/v) propyl propionate, and another stream, denominated coarse extract, of about 7,406 kg/h of a suspension containing PHB and water dissolved in the butyl acetate and insoluble residues of extracted biomass. The coarse extract is then continuously fed to a hydrocyclone, where the flow is separated in two streams: one stream about 75% the feeding flow in the upper part and containing about 35% the insoluble solids originally contained in the fed coarse extract; and another stream in the lower part of about 25% the fed flow and containing about 65% the insoluble solids originally contained therein. The upper stream of the hydrocyclone, poor in insoluble solids, is then fed to a membrane micro-filtration unit at a flowrate of 5,063 kg/h, generating a stream of about 844 kg/h (⅙) concentrated in residual insoluble solids of the extracted biomass, and a permeate stream of 4,219 kg/h (⅚) free of residual insoluble solids of the extracted biomass. The retention time in the process is of about 10 minutes. The stream rich in insoluble solids of the hydrocyclone (lower phase) and of the membrane are then mixed and sent to a filtration step, for example in plate filters, at a flowrate of 2,531 kg/h, generating a stream of about 2,380 kg/h, which is a PHB solution free of insoluble solids in suspension and a meal containing the insoluble solids of the extracted biomass of about 151.5 kg/h. The PHB recovery of the process is higher than 95% (weight/weight) in relation to the fed PHBV of the biomass, i.e., 70-80 kg of PHBV/h, depending on the biomass flow and purity. Both the filtrates obtained in the membrane and filter extraction process are rapidly cooled to a temperature which is equal to or lower than about 45° C., in order to guarantee the precipitation of PHBV in the solvent.

The Alcaligenes eutrophus biomass concentrated at 25% dry material and containing about 60%-75% PHB with a molecular weight of about 1,000,000 Da is fed to a mechanically agitated reactor, maintained at about 95-105° C. at a flowrate of 500 kg/h, in which it receives the addition of 8000 kg/h of propyl propionate heated at about 130° C. and propyl propionate vapor at 130° C., in a sufficient quantity to evaporate the excess of water contained in the slurry, generating a stream of about 1,230 kg/h of vapor composed of about 24% water and 76% propyl propionate, and another stream denominated coarse extract of about 8268 kg/h of a suspension containing PHB and water dissolved in the propyl propionate and insoluble residues of extracted biomass. The coarse extract is then continuously fed to a hydrocyclone, where the flow is separated in two streams: one stream of about 75% the feeding flow in the upper part and containing about 35% the insoluble solids originally contained in the fed coarse extract; and another stream in the lower part of about 25% the fed flow and containing about 65% the insoluble solids originally contained therein. The upper stream of the hydrocyclone, poor in insoluble solids, is then fed to a membrane micro-filtration unit at a flowrate of 6,201 kg/h, generating a stream of about 1,034 kg/h (⅙) concentrated in residual insoluble solids of the extracted biomass, and a permeate stream of 5,167 kg/h (⅚) free of residual insoluble solids of the extracted biomass. The retention time in the process is about 3-10 minutes. The stream rich in insoluble solids of the hydrocyclone (lower phase) and of the membrane are then mixed and sent to a filtration step, for example in plate filters, at a flowrate of 3,100 kg/h, generating a stream of about 2,850 kg/h, which is a PHB solution free of insoluble solids in suspension and a meal containing the insoluble solids of the extracted biomass of about 250 kg/h. The PHB recovery of the process is higher than 95% (weight/weight) in relation to the fed PHB of the biomass, i.e., 70-90 kg of PHB/h, depending on the biomass flow and purity. Both the filtrates obtained in the membrane and filter extraction process are rapidly cooled to a temperature which is equal to or lower than about 45° C., in order to guarantee the precipitation of PHB in the solvent.

Example 1.3.6

PHB Extraction and Recovery Using 1-Hexanol as Solvent in a One-Stage Extraction Test of Solubility of PHB in Hexanol:

To a 50 ml round bottom distillation flask, 31 g of concentrated biomass of Alcaligenes eutrophus containing 28.11% dry material and 16.09% PHB with a molecular weight of 1,000,000 Da and 250 g of hexanol were added. The suspension was then submitted, under agitation, to evaporation of the solvent and water, by using a heating blanket coupled to the distillation flask, the thus generated binary vapor being conducted to a straight tube condenser (Liebig type) for condensation and the resulting condensate collected in an Erlenmeyer recipient. The suspension was maintained in evaporation process under vigorous agitation until reaching the extraction temperature. The temperature was read in a mercury thermometer affixed to one of the flask nozzles and maintained in contact with the vapor phase inside the flask. The extraction temperature was reached after an evaporation time of about 15 minutes had elapsed, the boiling temperature of the mixture passing from about 104° C. (initial temperature) to about 133° C. (extraction temperature), in this period being generated about 34 ml of condensate consisting of about 44% (v/v) hexanol, the remaining volume being the water coming from the concentrated biomass. The suspension was then maintained in a condensate reflux regime under vigorous agitation for about 10 minutes at the temperature of 133° C. (extraction temperature), being subsequently filtrated, still heated, in filter paper, for separating the insoluble part from the part dissolved in the filtrated solvent. The heated filtrated material containing about 0.83% (p/p) of solubilized PHB was then cooled for precipitation of the PHB, was concentrated through filtration, submitted to evaporation of the solvent and subsequently to drying. The obtained PHB presented a molecular weight of about 430,000 DA. The quantity of concentrated biomass used in the tests was about 2.0-3.5 times greater than the necessary quantity to reach the concentration of PHB saturation in the solvent, at the employed extraction temperature. Thus, the concentration of saturation of the solute (PHB) in the solvent (hexanol) for the employed extraction temperature could be determined.

Test of PHB Extraction in Hexanol:

To a 500 ml round bottom distillation flask, 10 g of concentrated biomass of Alcaligenes eutrophus containing 28.11% dry material and 16.09% PHB with a molecular weight of 1,000,000 Da and 200 g of hexanol were added. The suspension was then submitted to evaporation of the solvent and water, by using a heating blanket coupled to the distillation flask, the thus generated binary vapor being conducted to a straight tube condenser (Liebig type) for condensation and the resulting condensate collected in an Erlenmeyer recipient. The suspension was maintained in evaporation process under agitation until reaching the extraction temperature. The temperature was read in a mercury thermometer affixed to one of the flask nozzles and maintained in contact with the vapor phase inside the flask. The suspension was then maintained in a condensate reflux regime and under agitation for about 10 minutes at the temperature of 133° C. (extraction temperature). The material thus obtained was then submitted to a process of heat decantation and the insoluble solid residue resulting from the extraction was separated from the PHB solubilized in the solvent. The solution containing dissolved PHB was cooled for precipitation of PHB and the PHB mass extracted in this stage was measured. The solid residue obtained in the first stage received the new addition of 200 g of hexanol and was again submitted to extraction for 10 minutes. The other procedures were repeated until totalizing three extraction stages. About 64.5% the PHB originally contained in the cellular biomass was extracted in the first stage, 19.0% in the second stage and 8.0% in the third stage. The molecular weight of the PHB thus obtained was within the range from 530,000 Da to 680,000 Da.

Example of Extrapolation to Industrial Scale

The Alcaligenes eutrophus biomass concentrated at 28.11% dry material and containing about 16.09% PHB and molecular weight of about 1,000,000 Da is fed to a mechanically agitated reactor, maintained at about 133° C. at a flowrate of 500 kg/h, in which it receives the addition of 10,019 kg/h of hexanol heated at about 133° C., in the liquid and in the vapor form and in a sufficient quantity to evaporate the excess of water contained in the slurry, generating a stream of about 542.6 kg/h of vapor composed of about 20% water and 60% (w/w) of hexanol, and another stream, denominated coarse extract, of about 9,997 kg/h of a suspension containing PHB and water dissolved in hexanol and insoluble residues of the extracted biomass. The coarse extract is then continuously fed to a hydrocyclone, where the flow is separated in two streams: one stream of about 75% the feeding flow in the upper part and containing about 35% the insoluble solids originally contained in the fed coarse extract; and another stream in the lower part of about 25% the fed flow and containing about 65% the insoluble solids originally contained therein. The upper stream of the hydrocyclone, poor in insoluble solids, is then fed to a membrane micro-filtration unit at a flowrate of 7,482 kg/h, generating a stream of about 1,247 kg/h (⅙) concentrated in residual insoluble solids of the extracted biomass, and a permeate stream of 6,235 kg/h (⅚) free of residual insoluble solids of the extracted biomass. The retention time in the process is of about 10 minutes. The stream rich in insoluble solids of the hydrocyclone (lower phase) and of the membrane are then mixed and sent to a filtration step, for example in plate filters, at a flowrate of 3,741 kg/h, generating a stream of about 3,90 kg/h, which is a PHB solution free of insoluble solids in suspension, and a meal containing the insoluble solids of the extracted biomass of about 151.5 kg/h. The PHB recovery of the process is higher than 95% (weight/weight) in relation to the fed PHBV of the biomass, i.e., 70-80 kg of PHBV/h, depending on the biomass flow and purity. Both the filtrates obtained in the membrane and filter extraction process are rapidly cooled to a temperature that is equal to or lower than about 45° C., in order to guarantee the precipitation of PHBV in the solvent.

Example 1.5

Partial Solvent Evaporation and Wash of the PHB Suspension in Isoamyl Alcohol for Obtaining Granule Aglomerates of High Porosity, which are Brittle and Easily Shearable The PHB suspension in a solution of isoamyl alcohol and water containing 4-10% PHB is fed to a vacuum evaporator at a flowrate of 1,000 kg/h, together with a water stream containing isoamyl alcohol dissolved at a flowrate of 500-1000 kg/h and recovered from the extraction and purification process. The mixture is then continuously submitted to evaporation through direct vapor injection in order to, simultaneously with the removal of solvent by evaporation, obtain a suspension containing solvent, water and agglomerates of PHB granules, which are continuously sheared through a mechanical device installed in the circulation pump of the system. The material resulting from this process is a suspension of PHB particles, finely divided in water and isoamyl alcohol dissolved therein, which is continuously removed from the system with a concentration of PHB particles in suspension of 4-20% (weight/weight) and sent to the next stage of solvent extraction.

Example 1.6

Extraction of Isoamyl Alcohol (Solvent) from the Suspension of Finely Divided PHB Particles with Simultaneous Wash and Comminution of the Product A suspension of finely divided PHB particles, obtained as exemplified in example 1.5, containing from 2 to 20% solids, is fed to an agitated reactor of solvent extraction (stripping) at a flowrate of 1000 kg/h, in which vapor is admitted by direct contact, as well as water, until removing isoamyl alcohol dissolved in the water, jointly with some water, which will form the effluent vapor phase of the system. Simultaneously with the evaporation of the residual isoamyl alcohol and continuously, the suspension of PHB particles in water is submitted to an additional shearing process through a device similar to that described in example 1.5. Upon completion of the solvent extraction process, there is obtained a PHB suspension in water, finely divided, substantially pure and free of solvent, in a concentration of 5-20% solids in suspension. This suspension is then cooled and conducted to a filtration step, in which is obtained a PHB meal of about 50-80% humidity which is subsequently dried.

The invention claimed is:
1. A process for recovering polyhydroxyalkanoates (PHAs) from a concentrated cellular biomass slurry of bacteria in an aqueous suspension obtained by a flocculation and concentration method comprising:
 providing a cellular biomass in suspension in a fermented culture medium,
 diluting the cellular biomass in water to form a fermented material to water ratio of up to about 1-3.0:1,
 acidifying the diluted cellular biomass to between pH 1.5 to about 5.5,
 adding an alkalizing agent to bring the pH of the biomass to between pH 7 and pH 12.0, and
 adding a flocculating agent to the alkalized solution to obtain flocculated biomass,
the process comprising the steps of:
 (i) injecting PHA solvent into the concentrated cellular biomass slurry while vigorously agitating the slurry;
 (ii) heating the slurry in the interior of a reactor to dissolve the PHA contained in the cellular biomass and form a suspension;
 (iii) separating the solvent, enriched with the dissolved PHA, from the suspension;
 (iv) rapidly cooling the PHA solvent solution enriched with PHA to a temperature which is sufficient to substantially precipitate all the dissolved PHA;
 (v) cold micro filtering the solvent solution at a temperature sufficient to precipitate the dissolved PHA;
 (vi) separating a concentrated paste of precipitated PHA from the micro-filtered solution;
 (vii) washing the paste concentrated with PHA with water, while heating and agitating the paste, to promote sufficient evaporation of solvent to form a suspension containing brittle PHA granules of high porosity;
 (viii) agitating the washed and heated PHA granules, while injecting water vapor into the suspension containing the remaining solvent and water, wherein the recovery rate of PHA particles is 90% or greater; and
 (ix) separating the purified PHA particles from the suspension wherein the cellular biomass is a biomass derived from any microorganism or plant, which can produce PHA naturally or by genetic modification.
2. The process as set forth in claim 1, wherein the PHA solvent used is selected from the group of solvents consisting of: butyl acetate, isobutyl acetate, amyl acetate, isoamyl acetate, isobutyl alcohol, 1-butanol, 1-pentanol (amyl alcohol), 2-methyl-1-butanol, 3-methyl-1-butanol, (isoamyl alcohol), 3-pentanol, 1-hexanol, cyclohexanol, propyl propionate, butyl propionate, isobutyl proprionate, ethyl butyrate, isobutyl isobutyrate, and mixtures of these solvents.
3. The process as set forth in claim 2, wherein the solvent used is isoamyl alcohol, or isomeric mixtures of isoamyl alcohol.
4. The process as set forth in claim 3, wherein the isoamyl alcohol is obtained by fractionizing fusel oil as a by product of the ethanol fermentation, the fusel oil being primordially composed by isoamyl alcohol and isomers thereof, besides impurities, such as: ethanol, n-propanol, isobutanol, n-butanol, and water.
5. The process as set forth in claim 4, wherein the PHA is selected from the group consisting of poly-3-hydroxybutyrate (PHB), poly(hydroxybutyrate-co-hydroxyvalerate) PHBV, and mixtures of these polymers and copolymers.
6. The process as set forth in claim 5, wherein the PHA is produced by bacterial fermentation, using microorganisms which are able to biosynthesize PHA using, as main raw material, sugars extracted from the sugarcane, and in that the main energetic source used to generate the thermal energy and the electric energy required by the process is the sugarcane bagasse.
7. The process as set forth in claim 1, wherein the PHA is selected from the group consisting of poly-3-hydroxybutyrate (PHB), poly(hydroxybutyrate-co-hydroxyvalerate) PHBV, and mixtures of these polymers and copolymers.
8. The process as set forth in claim 1, wherein the bacterial cellular biomass obtained through fermentation and to be processed is previously thermally inactivated.

9. The process as set forth in claim 1, wherein the step of injecting solvent into the concentrated cellular biomass slurry comprises operations of injecting liquid PHA solvent and PHA solvent in the form of vapor, in order to provoke the heating of the cellular biomass to a temperature between about 90° C. and the boiling temperature of the solvent at a substantially atmospheric pressure, and to form: a liquid phase comprising PHA solvent enriched with PHA and water remaining from the cellular biomass slurry; a solid phase defined by the insoluble residues of the residual cellular biomass; and a vapor phase containing vapors of water and of the PHA solvent.

10. The process as set forth in claim 9, wherein it comprises the additional step of extracting the vapor phase from the interior of the reactor.

11. The process as set forth in claim 10, wherein the PHA paste is washed with a water stream coming from the condensation of the vapor phase extracted from the reactor during the step of cellular rupture and PHA dissolution.

12. The process as set forth in claim 1, wherein the acidification of the diluted cellular biomass is obtained by adding an acid defined by at least one of the sulfuric and phosphoric acids.

13. The process as set forth in claim 1, wherein the alkalizing agent comprises calcium hydroxide.

14. The process as set forth in claim 1, wherein the acidification is carried out in order to obtain a pH from about 2.0 to about 3.0.

15. The process as set forth in claim 1, wherein the flocculated biomass is concentrated by at least one of the operations of decantation and centrifugation.

16. The process as set forth in claim 1, wherein the cellular biomass slurry is subjected to washing with water and concentrated to a concentration of the range of 18%-45% of dry cellular biomass.

17. The process as set forth in claim 16, wherein the step of washing and concentrating the cellular biomass slurry is achieved by simultaneously submitting the latter to a flow of water and to the effects of centrifugal force.

18. The process as set forth in claim 1, wherein the PHA solvent which is injected into the cellular biomass slurry is heated.

19. The process as set forth in claim 1, wherein the step of separating the PHA solvent enriched with PHA dissolved therein from the suspension formed inside the reactor comprises at least one of the operations of membrane micro-filtration and of filtration in precoat filters.

20. The process as set forth in claim 1, wherein the step of separating the PHA solvent enriched with PHA dissolved therein from the suspension formed inside the reactor comprises a step of subjecting said suspension to a separation by the effect of centrifugal force of low intensity.

21. The process as set forth in claim 20, wherein the centrifugal force of low intensity, which is used in the step of separating, from the PHA solution enriched with PHA dissolved therein, insoluble residues of the remaining biomass which are contained in the suspension formed inside the reactor, is obtained by means of hydro cyclones, producing a suspension with low concentration of said residues and another suspension concentrated with said residues.

22. The process as set forth in claim 21, wherein the suspension of low concentration of biomass insoluble residues which leaves the hydro cyclones is rapidly submitted to an additional separation step for completely removing the residues before being submitted to the cooling step.

23. The process as set forth in claim 22, wherein the additional separation step is effected by membrane micro-filtration, in order to produce a solution of PHA dissolved in the PHA solvent, free of insoluble residues, and a suspension concentrated in biomass insoluble residues and containing a fraction of PHA dissolved in the PHA solvent, water, ashes, and color compounds dissolved in the PHA solvent.

24. The process as set forth in claim 23, wherein the suspension concentrated in insoluble residues of cellular biomass is subjected to a filtration step, in order to produce a meal containing the biomass insoluble residues and a filtrated solution of PHA dissolved in the solvent, free of insoluble residues and which will be rapidly submitted to the cooling step.

25. The process as set forth in claim 23, wherein the solution of PHA dissolved in the PHA solvent and free of insoluble residues represents about 60-90% by weight of the suspension in micro-filtration, the suspension concentrated in residues of cellular biomass representing about 10-50% by weight of said suspension in micro-filtration.

26. The process as set forth in claim 21, wherein the suspension concentrated with biomass insoluble residues which leaves the hydro cyclones is submitted to a filtration step for separating the biomass insoluble residues before being submitted to the cooling step.

27. The process as set forth in claim 1, wherein the step of cold micro-filtrating the suspension of PHA precipitated in the PHA solvent is carried out in order to produce a PHA paste with a concentration of PHA from about 3.5% to 8.0% w/w.

28. The process as set forth in claim 1, wherein it further comprises the final step of drying the PHA particles separated from the aqueous medium from which the solvent is depleted.

29. The process as set forth in claim 1, wherein the water and PHA solvent vapors, which are generated in the several stages of the process, are condensed and separated in two liquid phases: one solvent-rich liquid phase which returns to the process in the PHA extraction and recovery step; and another solvent-poor liquid phase, which is recirculated in the process to allow recovering the PHA solvent contained therein.

30. The process as set forth in claim 1, wherein the PHA granules obtained in step (vii), after drying, have a particle average size in the range from 40 to 400 ppm and preferably in the range from 100 to 200 ppm.

31. A process for recovering polyhydroxyalkanoates (PHAs) from a cellular biomass of bacteria, said biomass being obtained by fermentation and by using a flocculating agent, in the form of a cellular biomass slurry in aqueous suspension, and with a dry cellular content not inferior to about 18% by weight, characterized in that it comprises the steps of:
  i) submitting the concentrated cellular biomass slurry to concomitant operations of injection of solvent, capable to dissolve PHAs, of vigorous agitation and of quick heating in the interior of a reactor, in order to provoke the rupture of the walls of the cellular biomass and the dissolution of the PHA contained in the latter, wherein the steps of heating the fermented cellular biomass, of rupturing the cell walls of said cellular biomass, and of dissolving the PHA contained in the latter are carried out in a total time that is sufficiently short to allow obtaining a PHA with a molecular weight at minimum of about 850,000 Da, from a biomass containing PHA with a molecular weight at minimum of about 1,000,000 Da, and to form a suspension comprising solvent, capable to dissolve PHAs, enriched with dissolved PHA, water remaining from the cellular biomass slurry and insoluble residues of the concentrated cellular biomass;
  ii) submitting the suspension formed in the reactor to a separation step, for recovering the solvent, enriched with the dissolved PHA, from the insoluble residues of the remaining cellular biomass;

iii) cooling the solution of the solvent capable to dissolve PHAs, enriched with PHA, in some seconds, by expansion, through heat exchange with another cooler stream or by means of heat exchangers, to a temperature which is sufficient to substantially precipitate all the dissolved PHA;

iv) micro-filtrating at 45° C. or less the PHA suspension precipitated in the solvent, capable to dissolve PHAs, containing water and impurities dissolved therein, in order to separate a concentrated paste of precipitated PHA;

v) submitting the paste concentrated with PHA to simultaneous operations of washing with water, heating and agitation, in order to promote the evaporation of a certain amount of solvent which is adequate to obtain a suspension containing PHA granules of high porosity and which are brittle and easily shearable, the remaining solvent, and water;

vi) submitting the washed and heated PHA granules to agitation and shearing, so as to rapidly break them, while processing the extraction of the residual solvent by injecting water vapor into the suspension containing the remaining solvent and water, in order to obtain purified PHA particles in the suspension; and vii) separating the purified PHA particles from the suspension.

32. The process of claim 1, wherein the flocculating agent is an anionic polyelectrolyte.

33. The process of claim 31, wherein the flocculating agent is an anionic polyelectrolyte.

* * * * *